US009121791B2

(12) United States Patent
Schulz et al.

(10) Patent No.: US 9,121,791 B2
(45) Date of Patent: Sep. 1, 2015

(54) HEAD ASSEMBLY FOR A MATERIAL TESTING MACHINE AND METHOD OF SERVICING THE SAME

(71) Applicant: MTS Systems Corporation, Eden Prairie, MN (US)

(72) Inventors: Bradley Dean Schulz, Savage (MN); Paul M. Krueger, Maple Grove, MN (US); Mark William Schletty, Richfield, MN (US); Tyler B. Kuhlmann, Minnetonka, MN (US); Richard Leo Taylor, Savage, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 13/835,972

(22) Filed: Mar. 15, 2013

(65) Prior Publication Data

US 2014/0102211 A1   Apr. 17, 2014

Related U.S. Application Data

(60) Provisional application No. 61/649,918, filed on May 21, 2012.

(51) Int. Cl.
*G01N 3/00*   (2006.01)
*G01N 3/62*   (2006.01)

(52) U.S. Cl.
CPC ... *G01N 3/00* (2013.01); *G01N 3/62* (2013.01)

(58) Field of Classification Search
CPC ................................. G01N 3/62; G01N 3/00
See application file for complete search history.

(56) References Cited

U.S. PATENT DOCUMENTS

| 6,643,599 | B1 | 11/2003 | Mohr |
| 2008/0289395 | A1 | 11/2008 | Torng |
| 2009/0199663 | A1* | 8/2009 | Kaneda ........................... 73/866 |

FOREIGN PATENT DOCUMENTS

| CH | 703946 | 4/2012 |
| WO | 2008023226 | 2/2008 |

OTHER PUBLICATIONS

Communication Relating to the Results of the Partial International Search for corresponding PCT/US2013/041998, filed May 21, 2013.
International Search Report and Written Opinion from corresponding PCT/US2013/041998, international filing date May 21, 2013.

* cited by examiner

*Primary Examiner* — Lisa Caputo
*Assistant Examiner* — Brandi N Hopkins
(74) *Attorney, Agent, or Firm* — Steven M. Koehler; Westman, Champlin & Koehler, P.A.

(57) ABSTRACT

A testing machine includes a pair of vertical columns, a crosshead selectively positionable on the vertical columns, and a head assembly supported by and movable with the crosshead. The head assembly has an electric actuator, a support that can be selectively moved from a first position when the test machine is operated to a lowered position. The support supporting components are related to powering or controlling the electric actuator, said components are exposed for servicing in the lowered position.

20 Claims, 8 Drawing Sheets

HEAD ASSEMBLY FOR A MATERIAL TESTING MACHINE AND METHOD OF SERVICING THE SAME

CROSS-REFERENCE TO RELATED APPLICATION

The present application is based on and claims the benefit of U.S. provisional patent application Ser. No. 61/649,918, filed May 21, 2012, the content of which is hereby incorporated by reference in its entirety.

BACKGROUND

The discussion below is merely provided for general background information and is not intended to be used as an aid in determining the scope of the claimed subject matter.

Aspects of the present invention relate to test machines or apparatus used to test parameters and/or performance of materials, components, consumer products, electronics, materials, as well as medical and other devices (i.e. test specimens).

SUMMARY

A testing machine includes a pair of vertical columns, a crosshead selectively positionable on the vertical columns, and a head assembly supported by and movable with the crosshead. The head assembly has an electric actuator, a support that can be selectively moved from a first position when the test machine is operated to a lowered position. The support supporting components are related to powering or controlling the electric actuator, said components are exposed for servicing in the lowered position.

DETAILED DESCRIPTION OF ILLUSTRATIVE EMBODIMENTS

Figure 1:
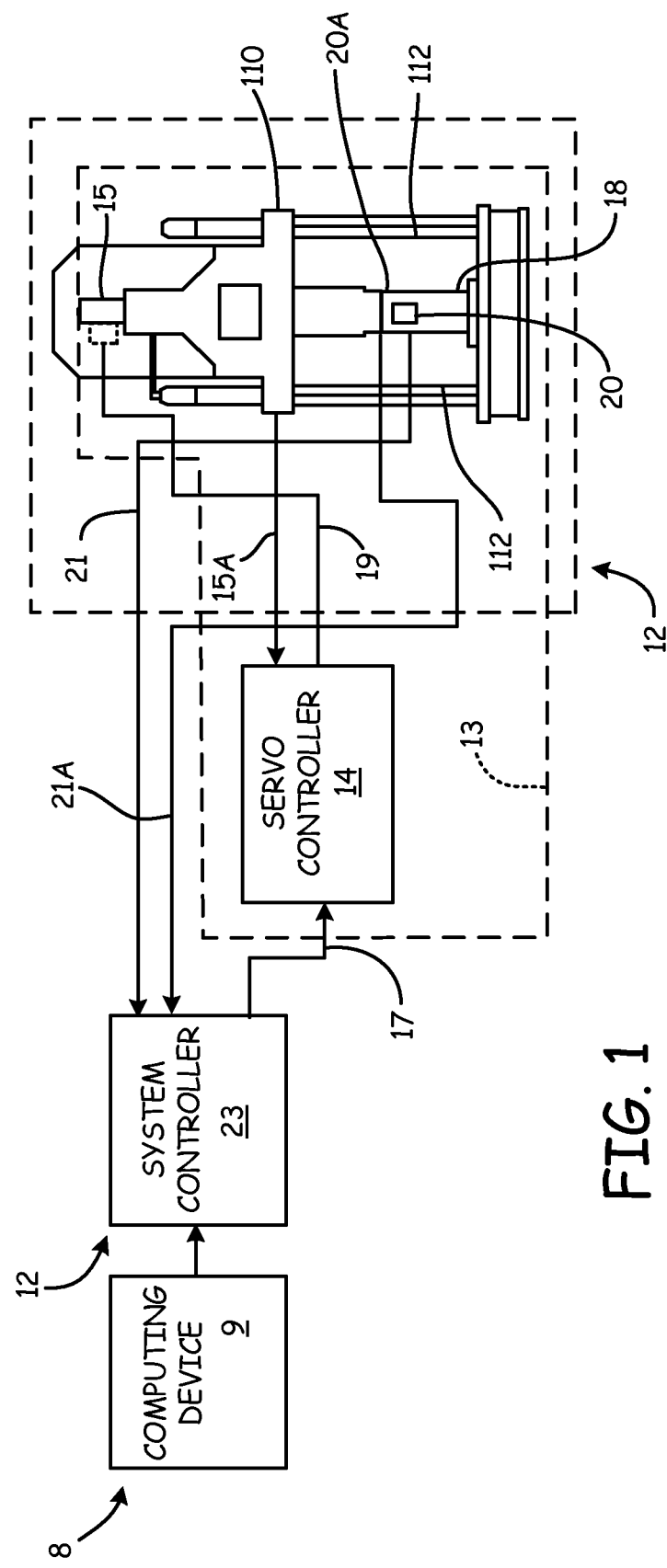
FIG. 1 is a schematic illustration of a process control loop for controlling operation of a test apparatus.

In the exemplary embodiment of FIG. 1, a testing machine system 8 comprising a computing device 9, test machine 12 and a system controller 23 are illustrated. The testing machine 12 includes an electric actuator system 13 having an electric actuator 15 and a controller or drive 14 therefor. The controller 14 provides an actuator command signal 19 to operate the actuator 15 having a movable actuator rod 22, which in turn, excites a test specimen 18. Suitable feedback 15A can be provided from the actuator 15 to the controller 14 or from other sensors. One or more remote transducers 20 on the test specimen 18 or physical system 10, such as displacement sensors, strain gauges, accelerometers, load cells, thermometers or the like, provide a measured or actual response 21. In the exemplary embodiment, a load cell 20A also provides a response 21A.

A system controller 23 receives actual response 21 as feedback in a response to a drive 17 as input to the controller 14. In the illustration of FIG. 1, signal 17 is a reference signal, signal 19 is a manipulated variable (command to actuated device) and signal 15A is a feedback variable. The test specimen 18 can take any number of forms such as but not limited to material samples, substructures or components. Typically, types of loads that can be applied or imparted to the test specimen 18 include tension, compression and/or torsion in one or more degrees of freedom applied separately or at the same time. The test specimen 18 can also or alternatively be subjected to controlled displacements in one or more degrees of freedom applied separately or at the same time. Computing device 9 commonly receives the data and is used to analyze the data.

Figure 2:
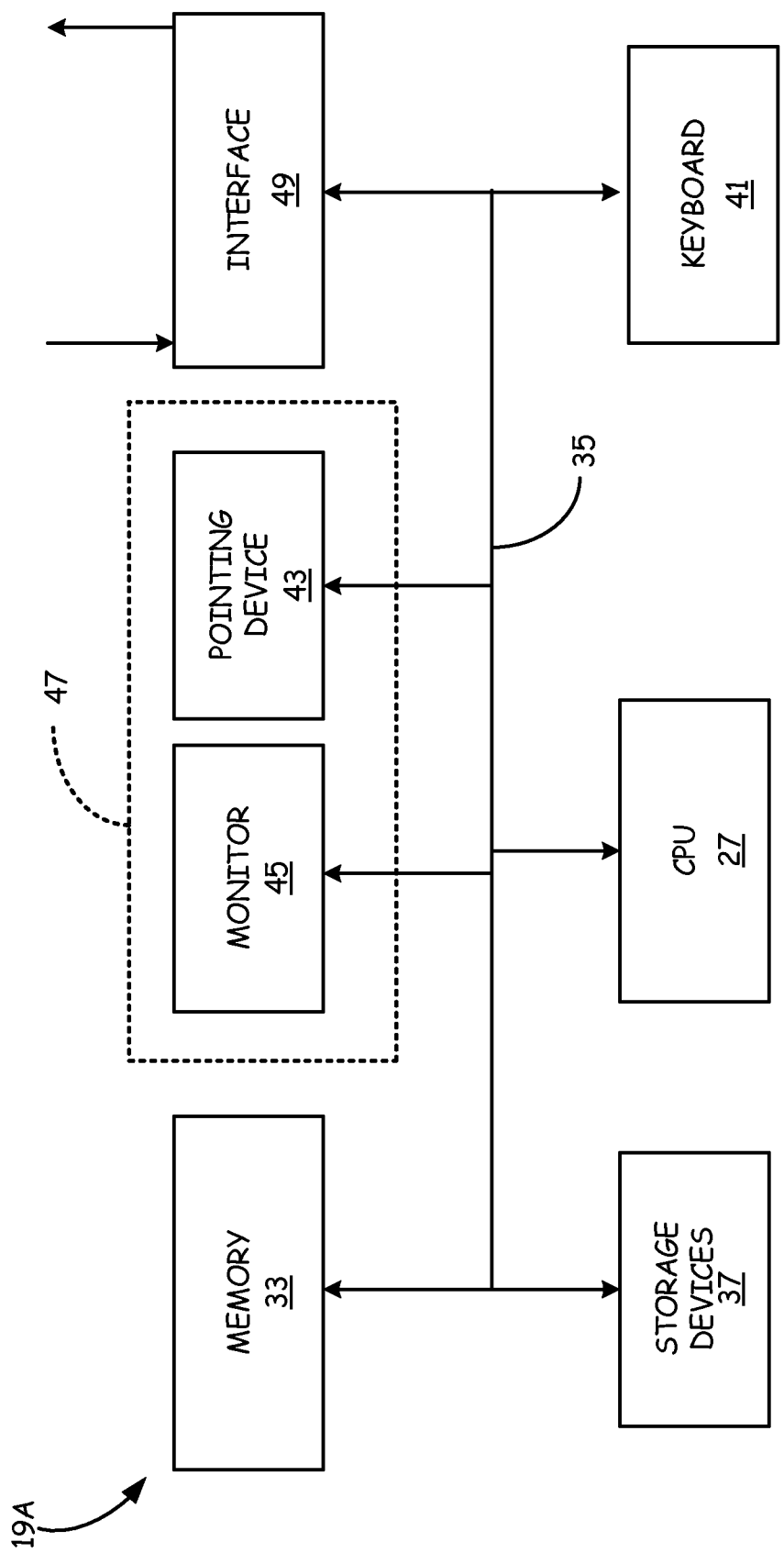
FIG. 2 is a block diagram depicting certain components of a computing device.

The computing device 9, controller 14 and system controller 23 can each be implemented on a digital computer. FIG. 2 and the related discussion provide a brief, general description of a suitable computing environment in which the computing device 9, controller 14 and system controller 23 may each be implemented. Computer 19A has program modules including routine programs, objects, components, data structures, etc., which perform particular tasks or implement particular abstract data types. Those skilled in the art can implement the description below and/or diagrams to computer-executable instructions storable on a computer readable medium. Moreover, those skilled in the art will appreciate that the invention may be practiced with other computer system configurations, including multi-processor systems, networked personal computers, mini computers and the like.

The computer 19A illustrated in FIG. 2 comprises a conventional computer having a central processing unit (CPU) 27, memory 33 and a system bus 35, which couples various system components, including memory 33 to the CPU 27. System bus 35 may be any of several types of bus structures including a memory bus or a memory controller, a peripheral bus, and a local bus using any of a variety of bus architectures. The memory 33 includes read only memory (ROM) and random access memory (RAM). A basic input/output (BIOS) containing the basic routine that helps to transfer information between elements within the computer 19A, such as during start-up, is stored in ROM. Storage devices 37, such as a hard disk, a floppy disk drive, an optical disk drive, etc., are coupled to the system bus 35 and are used for storage of programs and data. It should be appreciated by those skilled in the art that other types of computer readable media that are accessible by a computer, such as magnetic cassettes, flash memory cards, digital video disks, random access memories, read only memories, and the like, may also be used as storage devices. Commonly, programs are loaded into memory 33 from at least one of the storage devices 37 with or without accompanying data.

Input devices such as a keyboard 41 and pointing device (mouse) 43, simple switches or the like, allow the user to provide commands to the computer 19A. A monitor 45 or other type of output device display is further connected to the system bus 35 via a suitable interface and provides feedback to the user. If the monitor 45 is a touch screen, the pointing device 43 can be incorporated therewith.

Interfaces 49 on each of the computing device 9 and system controller 23 allow communication between the computing device 9 and the system controller 23 Likewise, interface circuitry 49 on each of the system controller 23 and the controller 14 allow communication between the system controller 23 and the controller 14. Interface circuitry 49 also represents circuitry used to send signals 19 or receive signals 15 and 21 as described above as well as other parameters of the physical system such as the status of locks, doors, indicators, whether power is applied, etc. Commonly, such circuitry comprises digital-to-analog (D/A) and analog-to-digital (A/D) converters as is well known in the art. The controller 14 can also comprise an analog controller with or without digital supervision as is well known. Functions of computing device 9, controller 23 and controller 14 can be combined into one computer system. In another computing environment, controller 14 is a single board computer operable on a network bus of another computer, which could be controller 23 or another supervisory computer. The schematic diagram of FIG. 2 is intended to generally represent a computer for these and other suitable computing environments.

Figure 4:
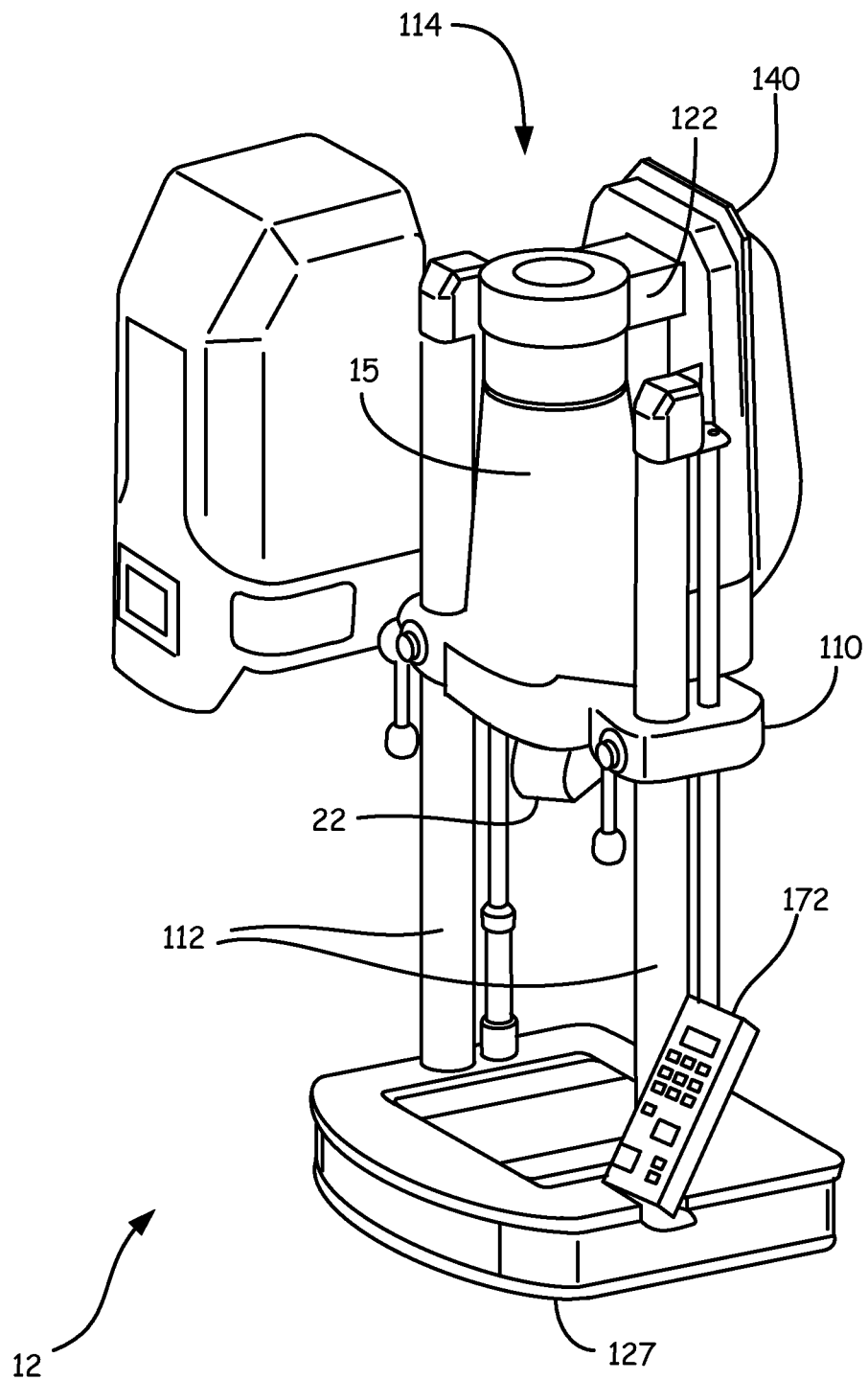
Figure 4A:
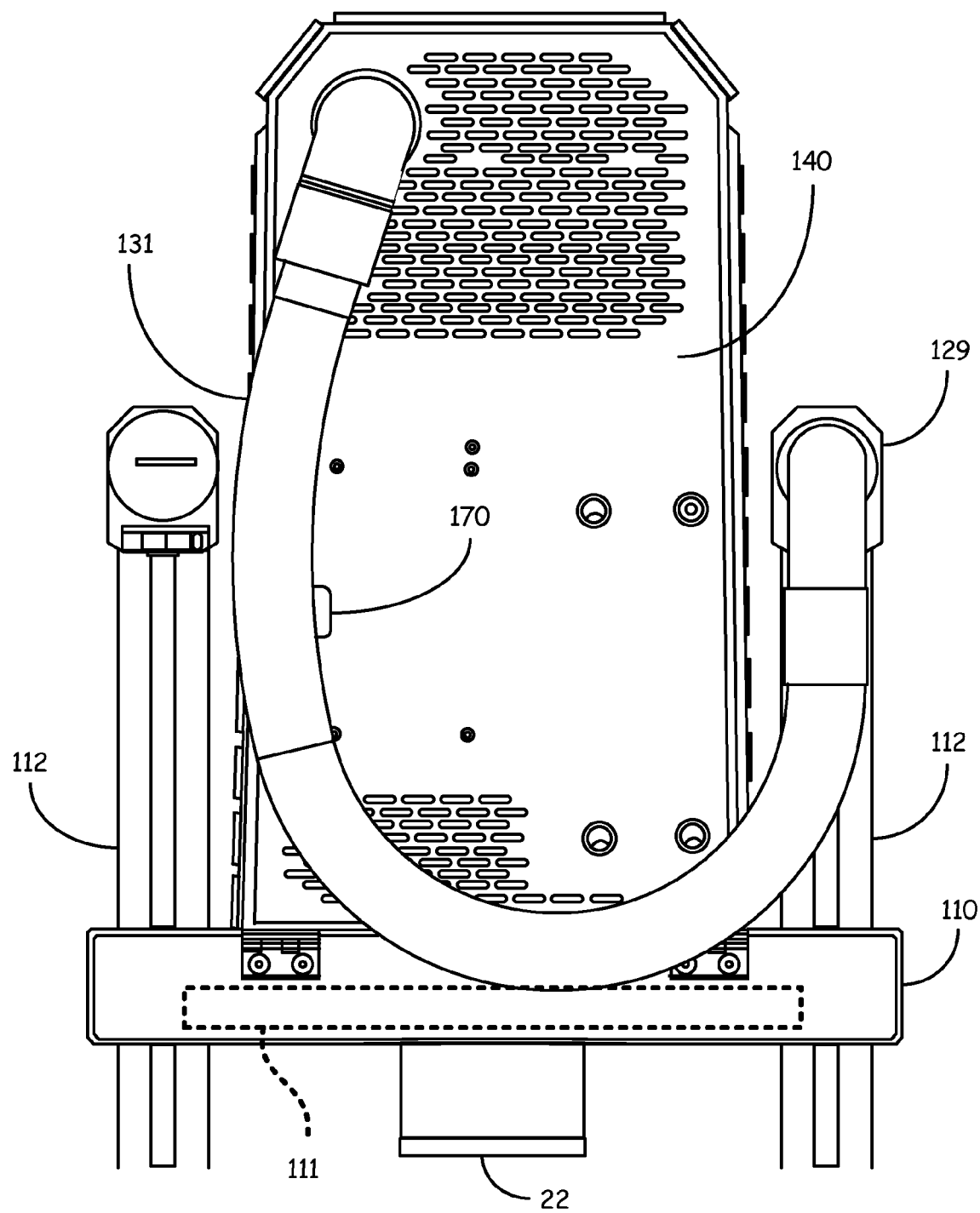
FIG. 4A is a back view of a support.
Figure 5:
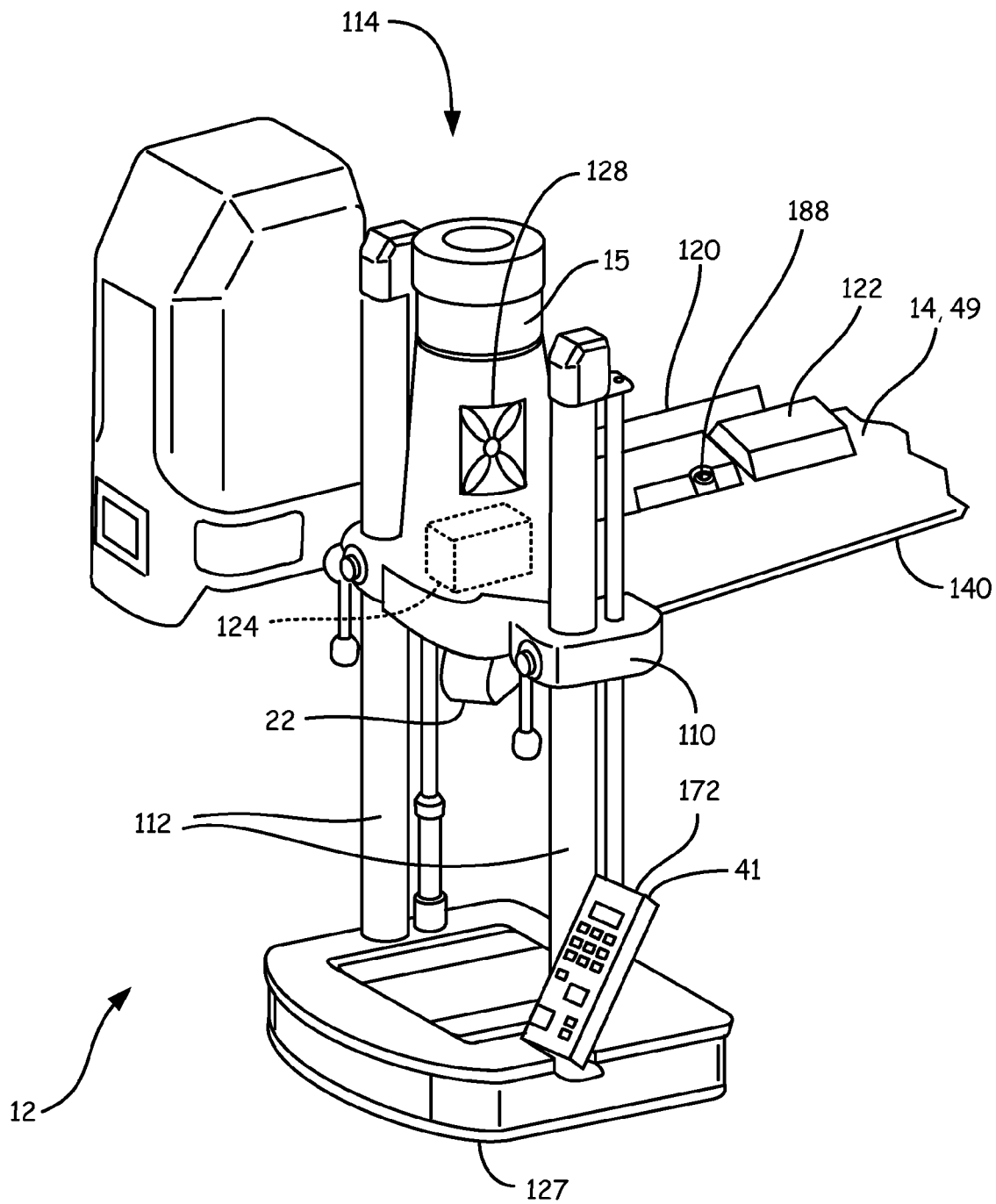

In the exemplary embodiment of FIG. 1, the testing machine 12 includes a crosshead 110 that is movable on vertical columns 112 by an electric crosshead drive (motor, gear reducer, drive belts, etc.) illustrated collectively and schematically at 111 in FIG. 4A, which is disposed in the crosshead 110. The details of crosshead drive 111 ich are not necessary for understanding aspects of the present invention. The crosshead drive 111 positions the crosshead where desired relative to the vertical columns 112 upon commands from the user. Referring to FIG. 5, the crosshead 110 supports a head assembly 114, which generally houses actuator 15, controller 14, power supply or supplies (e.g. a high voltage supply 120 for the actuator 13, a low voltage supply 122 for controller 14, sensors and/or interface circuitry 49). Locks selectively clamp the crosshead 110 to the vertical columns 112 so as to provide a rigid reaction structure. An electrically operated brake (schematically illustrate at 124 in FIG. 6) can hold the actuator rod 22 when desired, the details of which are not related to the aspects of the invention described herein. Typically, the brake is electrically actuated to release or disengage it from the actuator rod 22.

Location of the power supplies 120, 122, the electric actuator 15, controller 14 and/or other components to control the electric actuator 15 along with a cooling fans (schematically indicated at 128 as maybe needed) within the head assembly 114 is particularly advantageous because the footprint of the testing machine 12 is reduced in that additional, separate component enclosures (such as for one or more of the power supplies, motor drives, etc. which are typically separately cooled within the enclosures they are mounted) are not needed. Rather, only a single power connection 130 to source power 132 from the facility (e.g. laboratory), whereby intermediate power cabling to supply power from the separate power enclosures to the testing machine is not needed. Instead, only low voltage signal cabling 135 exists connecting the testing machine 12 to the system controller 23 (optionally with or in turn connected to computing device 9). The footprint or floor space savings are compounded when a plurality of testing machines 12 are present in the laboratory. It should be noted a single system controller 23 can control a plurality of testing machines 12.

Figure 3:
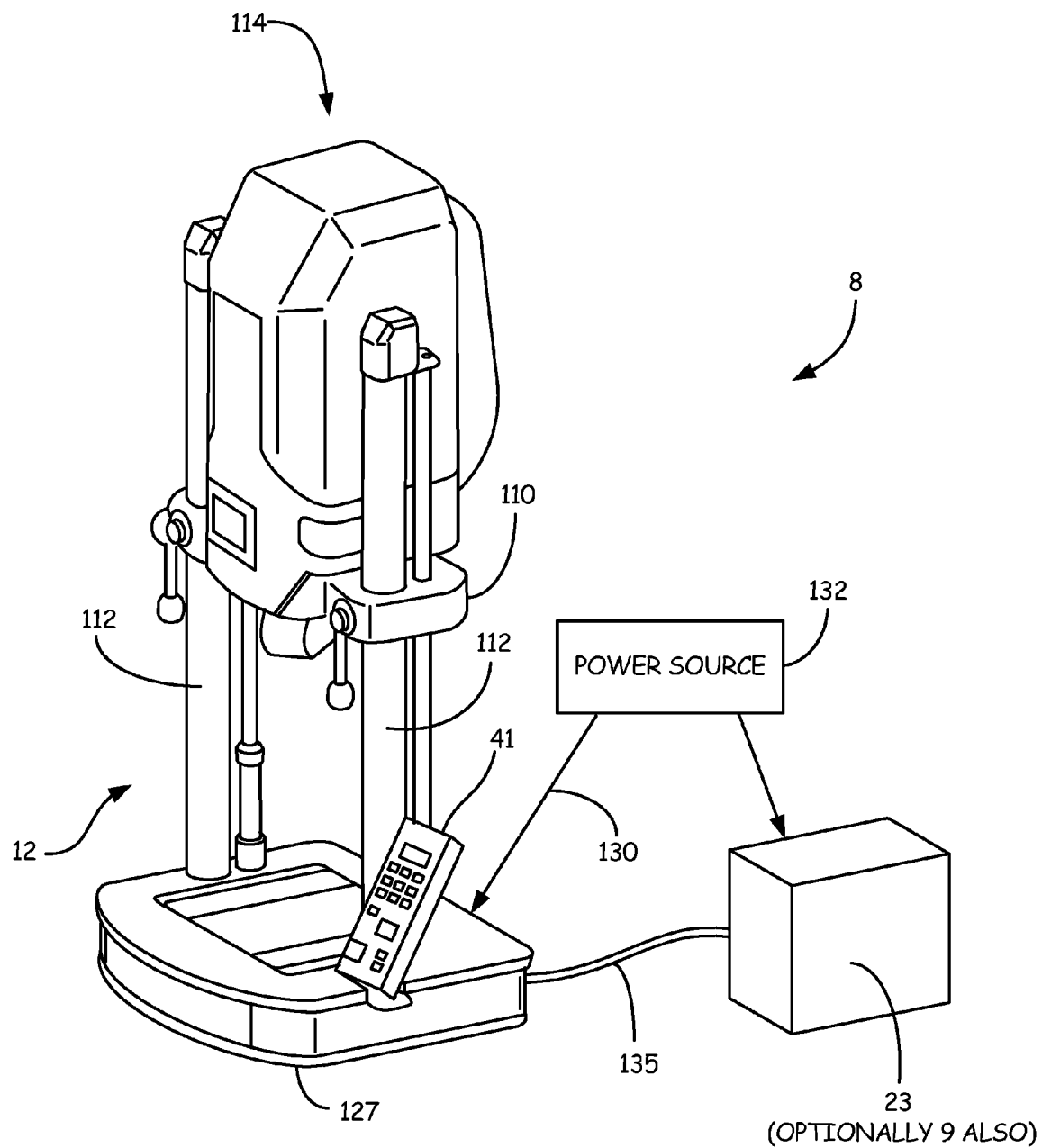
FIGS. 3, 4, 5 and 6 illustrate configurations of a head assembly.

In the embodiment particularly illustrated in FIGS. 3 and 4A, power and signaling cabling for components in the head assembly 114 extend from a base 127 up one of the vertical support columns 112 to a top portion 129 thereof whereat a flexible tubing 131 runs the power and signaling cabling from the portion 129 to the head assembly 114. The flexible tubing 131 conveniently contains all the cabling while allowing the head assembly 114 to move relative to the columns 112.

Another aspect herein disclosed is the ability to conveniently service the testing machine 12, and in particular, the head assembly 114. Comparing FIGS. 4 and 5, it can be seen that the head assembly 114 includes a (e.g. hinged) support 140 that can be selectively lowered allowing easy access to those afore-mentioned components mounted to the support 140. In the exemplary embodiment, the support 140 mounts the controller 14 and/or interface board 49, high voltage power supply 120, low voltage supply 122 and some electrical drive circuitry for the electric actuator 15. It should be understood the present invention is not limited to a support 140 that supports all the afore-mentioned components, but rather, in a preferable embodiment at least some are disposed on the support 140. Repositioning of the support 140 is particularly convenient because in a lowered (preferably, horizontal position, the support 140 conveniently positions those components mounted thereto at a height comfortable for servicing (such as at waist high for a service person). In addition, since the support 140 can reposition to and from a horizontal, working/servicing position of components to a vertical, storage or operating position of the testing machine 12, the width of the head assembly 114 can be narrower or less deep since the components mounted to the support 116 are arranged vertically rather than horizontally in the operating position.

It should be noted that tilting of the support 140 is but one technique for positioning the head assembly 114 and components therein in a more convenient location for servicing. Generally, simply positioning of the head assembly 114 in a lower position, for example, a waist high position of the user, is a great improvement, and doing so, as discussed below, without the necessity of the system controller 23 being connected is particularly advantageous since the "service mode" does not require another component of the testing machine system 8 to be functioning.

It should also be noted that repositioning components from an "operating position" where such components are positioned during operation of the test machine 12 to a "service position" can be accomplished with other techniques. For example, support panel 140 could be hinged to operate like a cabinet door and where, if desired, the aforementioned component(s) can be mounted to the inside surface of the cabinet door, and thereby be exposed when the door is opened. In yet another embodiment, component(s) can be mounted to a slidable panel(s) that can be pulled out at least partially to allow easier access to the component(s) on the slidable panel(s) as well as those remaining in the head assembly. Although illustrated where access to the components is from the rear, it should also be understood any of the afore-mentioned techniques can be performed from the front of the machine in the alternative to access from the rear, or in addition to access from the rear.

Figure 6:
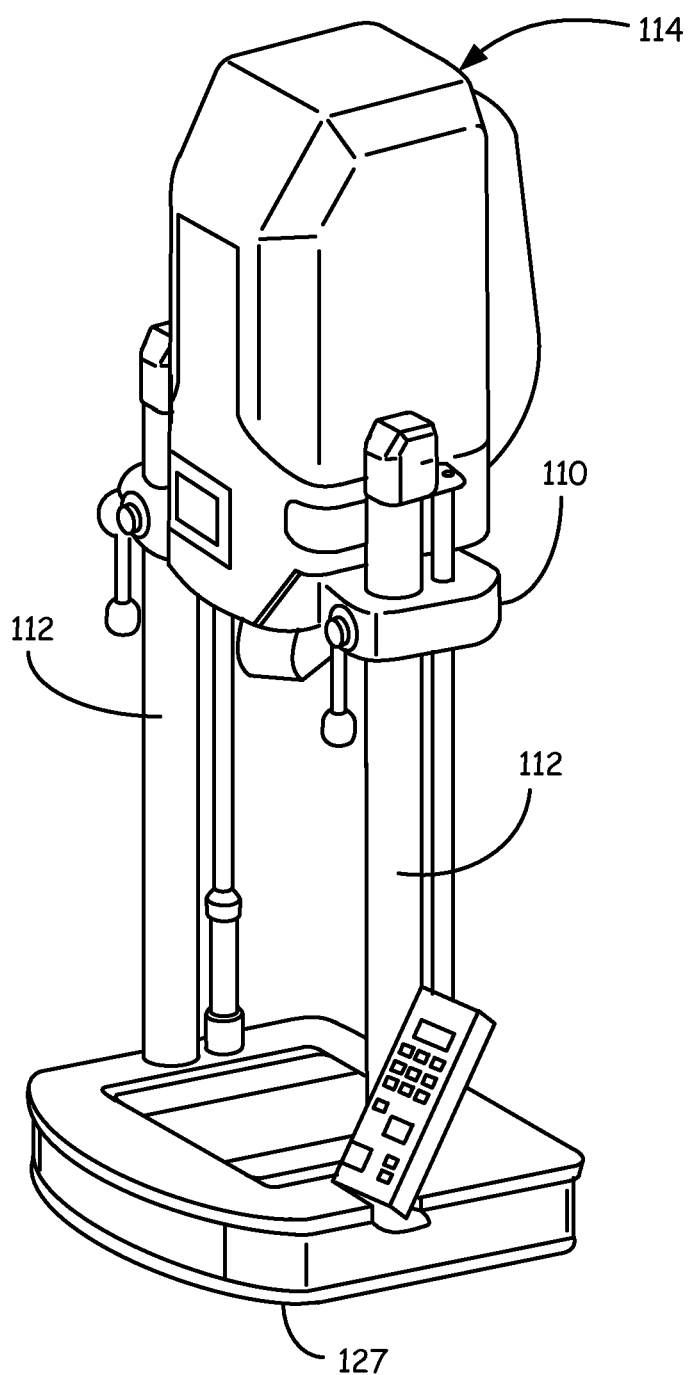
Figure 7:
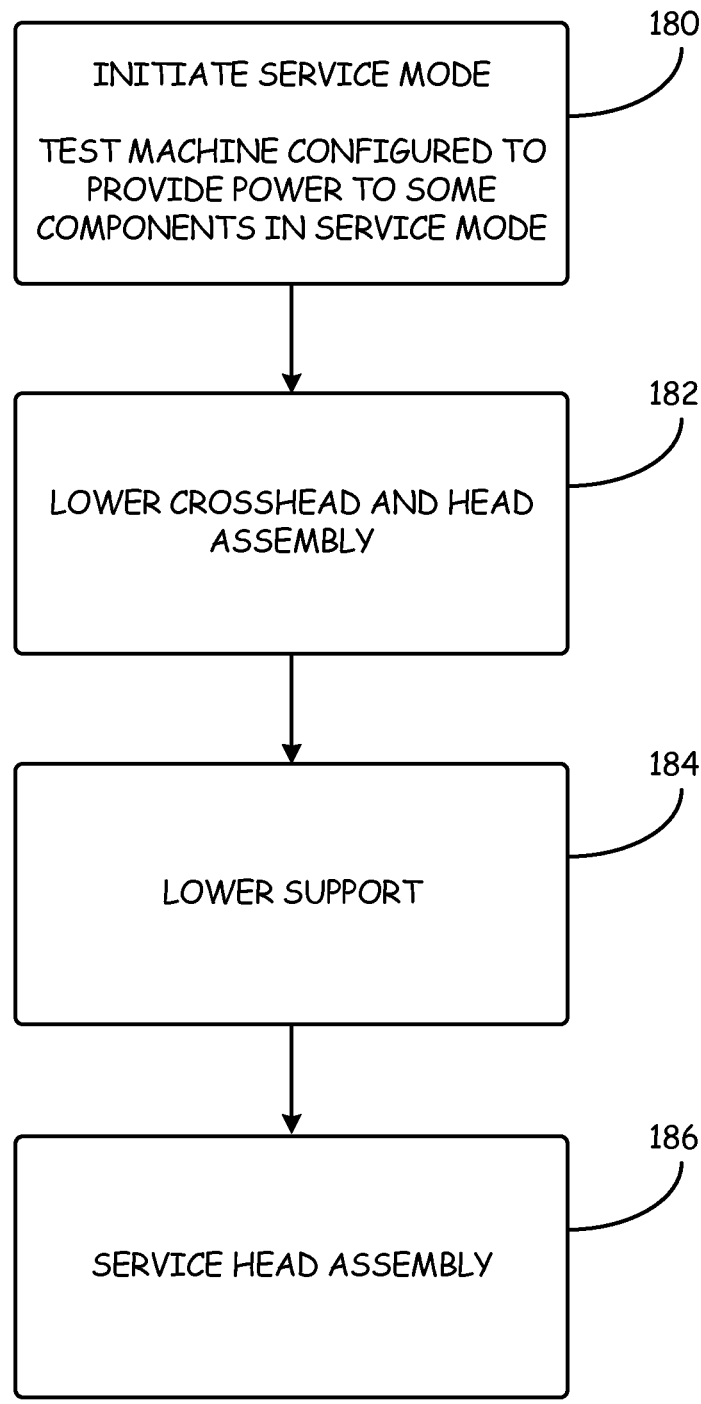
FIG. 7 illustrates a method of servicing the head assembly.

Another aspect allowing convenient servicing of the testing machine 12, and in particular, the head assembly 114 is that the head assembly 114 can be lowered from a generally inconvenient higher position to the convenient position of FIG. 5. FIG. 6 illustrates the head assembly 114 disposed high on the vertical columns 112. The user can reposition the head assembly 114 from the position in FIG. 6 to that of FIG. 3 particularly when the system controller 23 is not connected to the testing machine 12. In a further advantageous embodiment, the user can do so by also configuring the testing machine 12 to provide power only to certain components, the state of testing machine 12 being referred to herein as "service mode". Referring to FIG. 4A and FIG. 7, service mode as indicated by step 180 and is initiated by the user by activating switch 170 disposed on the support 140, which is exposed on the backside of the head assembly 114 when the support 140 is in the operating position. In an alternative embodiment, service mode could be initiated by a button or button sequence on a control panel 172 on testing machine that functions as an input device 41.

Upon activation of service mode, the test machine 12 only powers selective components. In one embodiment, the test machine 12 does not energize the actuator 15 nor supply power to the high voltage power supply 120; however, power is available to the crosshead drive for crosshead 110 such that the user can lower the crosshead 110 to a convenient height. Control of such power can be electronic circuitry, relays or the like. Lowering of the crosshead 110 is indicated by step 182 and can be performed using control panel 172 where control panel 172 functions as an input device for controller 14 or another controller/interface board on testing machine 12 that allows operation of the crosshead drive 111. Again, this can be accomplished without the need to have the testing machine 12 operably connected or otherwise in communication with the system controller 23, but rather only needing to be connected to power source 132. It should be noted that configuration of a testing machine to have a "service mode" that allows the head assembly to be lowered (or raised) relative to the vertical columns is not limited to a testing machine where the actuator 15 and/or power electronics are located in the head assembly 114. Rather, repositioning of the head assembly 114 for testing machines where the actuator 15 and/or power electronics is disposed in or on base 127 can also be advantageous. In particular, the head assembly and/or crosshead include serviceable components that can benefit by being placed in a lowered, for example, waist high position. Like the exemplary test machine 12 herein described, repositioning of the crosshead/head assembly of any testing machine is particularly convenient when the testing machine does not need to be operably connected to the system controller 23, again where repositioning is enabled through a user control device on the testing machine. Similarly also, it can also be advantageous to reposition the head assembly/crosshead when other components such as high voltage power supplies, drives and/or actuators are not powered.

In the lowered position on the vertical columns 112, the support 140 can be disposed to the lowered, (e.g. horizontal) position indicated at 184. In the embodiment illustrated, the ability to lower the support 140 can be a function of removal of a front cover 174.

As described above, servicing can be conducted at step 186 when the support 140 is in the lowered position.

In addition to any or all of the other limited components listed above that receive power, one other component that can be selectively operated is the electric brake 124, which engages the actuator rod 22 and inhibits movement thereof unless the brake is energized or powered. Again, without the need to have the testing machine 12 operably connected or otherwise in communication with the system controller, but rather only needing to be connected to power source 132, the user can energize the brake 124 by activation of a switch 188 disposed within the head assembly 114 and accessible when the support 140 is in the lowered position.

Although the subject matter has been described in language specific to structural features and/or methodological acts, it is to be understood that the subject matter defined in the appended claims is not necessarily limited to the specific features or acts described above as has been held by the courts. Rather, the specific features and acts described above are disclosed as example forms of implementing the claims.

What is claimed is:

1. A testing machine comprising:
   a support member;
   a crosshead selectively positionable on the support member; and
   a head assembly supported by and movable with the crosshead, the head assembly comprising an enclosure having an electric actuator at least partly therein and a door configured to provide an opening in the head assembly, a support that is movable selectively from a first position in the head assembly when the test machine is operated and the door is closed to a second position, the support supporting components related to powering or controlling the electric actuator, said components be exposed for servicing in the second position.

2. The testing machine of claim 1 wherein the second position of the support is a horizontal position.

3. The testing machine of claim 2 wherein the first position of the support is a vertical position.

4. The testing machine of claim 1 wherein the second position is a waist high position of a user standing next to the testing machine.

5. The testing machine of claim 1 wherein the support tilts from the first position to the second position.

6. The testing machine of claim 5 wherein the support moves with the door.

7. The testing machine of claim 5 and further comprising:
   a controller configured to operate the actuator;
   a drive connected the crosshead to selectively move the crosshead on the support member; and
   an input device separate from controller and configured to operate the drive, when the controller is disconnected from the testing machine.

8. The testing machine of claim 6 wherein the second position is a waist high position of a user standing next to the testing machine.

9. The testing machine of claim 8 and further comprising:
   a controller configured to operate the actuator;
   a drive connected the crosshead to selectively move the crosshead on the support member; and
   an input device separate from controller and configured to operate the drive, when the controller is disconnected from the testing machine so as to not operate the acutator.

10. The testing machine of claim 1 wherein the controllable movable element is an electric actuator and at least one component mounted to the support is a power supply or controller for the electric actuator.

11. The testing machine of claim 1 wherein the support member comprises a vertical support column.

12. The testing machine of claim 1 wherein the support member comprises a pair of vertical support columns, the crosshead being mounted to each of the vertical support columns, the crosshead supporting the head assembly.

13. A testing machine comprising:
    a pair of vertical columns;
    a crosshead selectively positionable on the vertical columns;
    an actuator;
    a controller configured to operate the actuator and apply load to a test specimen; and
    a drive connected to the crosshead to move the crosshead on the vertical columns, and
    an input device separate from the controller and configured to operate the drive, when the controller is disconnected from the testing machine so as to operate the actuator.

14. The testing machine of claim 13 and further comprising a head assembly mounted to the crosshead.

15. The testing machine of claim 14 wherein the head assembly includes a support for supporting components used for power or control of the actuator, the support movable from a first position whereat the components are not accessed for service to a second position whereat the components are accessed for service.

16. The testing machine of claim 15 wherein the second position of the support is a horizontal position.

17. The testing machine of claim 16 wherein the first position of the support is a vertical position.

18. The testing machine of any one of claim 13 wherein the drive is configured to selectively position the head assembly to a waist high position of a user standing next to the testing machine when the controller is disconnected from the testing machine.

19. A method for operating a testing machine to place a head assembly in a service position, the testing machine further comprising a base, a support member coupled to the head assembly, a drive for moving the head assembly to the service position relative to the base, and a controllable movable element, the method comprising:
   operating an input device to place the test machine in a service mode, the service mode being when selected components of the testing machine can receive power to operate;
   moving the head assembly to a service position, the service position being a lower position than a highest position of the head assembly relative to the base.

20. The method of claim 19 wherein the service position is a waist high position of a user standing next to the testing machine.

\* \* \* \* \*